United States Patent [19]

Fox et al.

[11] 4,307,098
[45] Dec. 22, 1981

[54] PESTICIDAL COMPOSITIONS AND PROCESSES FOR TREATING PLANTS

[75] Inventors: Roland T. V. Fox, Crowthorne, England; Gustave K. Kohn, Palo Alto, Calif.; William G. Rathmell, Wokingham; Margaret C. Shephard, Maidenhead, both of England

[73] Assignees: Imperial Chemical Industries Limited, London, England; Zoecon Corporation, Palo Alto, Calif.

[21] Appl. No.: 103,514

[22] Filed: Dec. 12, 1979

[30] Foreign Application Priority Data

Dec. 14, 1978 [GB] United Kingdom ............... 48455/78

[51] Int. Cl.³ ............................................ A01N 43/54
[52] U.S. Cl. ................................................... 424/251
[58] Field of Search .......................................... 424/251

[56] References Cited

U.S. PATENT DOCUMENTS

| | | | |
|---|---|---|---|
| 3,124,580 | 3/1964 | Surrey et al. | 424/251 |
| 3,266,993 | 8/1966 | Bardos | 424/251 |
| 3,923,807 | 12/1975 | Furukawa et al. | 424/251 |
| 3,971,784 | 7/1976 | Tada | 424/251 |
| 4,017,626 | 4/1977 | Gauri | 424/251 |
| 4,020,070 | 4/1977 | Gauri | 424/251 |

FOREIGN PATENT DOCUMENTS 2729161 4/1979 Fed. Rep. of Germany ...... 424/251
2730201 4/1979 Fed. Rep. of Germany ...... 424/251

Primary Examiner—Douglas W. Robinson
Attorney, Agent, or Firm—Cushman, Darby & Cushman

[57] ABSTRACT

A method and pesticidal composition for the preventative, protectant, prophylactic and eradicant treatment of plant fungi and bacteria comprises applying an effective amount to plants or seeds of a pesticidal composition containing in an inert carrier a compound of the formula

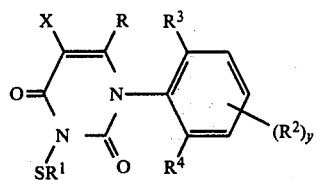

wherein R is hydrogen, methyl or ethyl; $R^1$ is polyhaloalkyl or polyhalovinyl; $R^2$ is lower alkyl, lower alkoxy, bromo, chloro, fluoro, lower haloalkyl, cyano, nitro, lower alkylthio, lower alkylcarbonyl, lower alkoxycarbonyl or cycloalkyl; $R^3$ is hydrogen or independently selected from the values of $R^2$; $R^4$ is hydrogen or independently selected from the values of $R^2$; X is hydrogen, carbamoyl or cyano; and y is zero, one or two.

6 Claims, No Drawings

PESTICIDAL COMPOSITIONS AND PROCESSES FOR TREATING PLANTS

This invention relates to pesticidal compositions containing, as an active ingredient, a 1-phenyl-3-polyhaloalkyl or -polyhalovinyl uracil and to methods of combating plant pests, especially fungi and bacteria, using them.

The invention provides a pesticidal composition comprising as an active ingredient a 1-phenyl-3-polyhaloalkyl or -polyhalovinyl uracil having the following formula A:

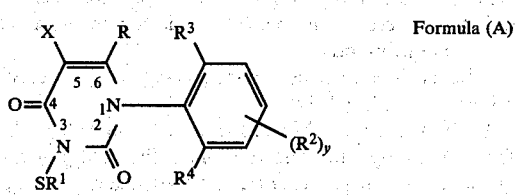

Formula (A)

wherein R is hydrogen, methyl or ethyl; $R^1$ is polyhaloalkyl or polyhalovinyl; $R^2$ is hydrogen, lower alkyl, lower alkoxy, bromo, chloro, fluoro, lower haloalkyl, cyano, nitro, lower alkylthio, hydroxy, lower alkylcarbonyl, lower alkoxycarbonyl, lower haloalkoxy, cycloalkyl, or cycloalkalkyl; $R^3$ is hydrogen or independently selected from the values of $R^2$; $R^4$ is hydrogen or independently selected from the values of $R^2$; X is hydrogen, carbamoyl, or cyano; y is zero, one, two or three.

The term "polyhaloalkyl", as used herein, refers to polyhalomethyl and polyhaloethyl wherein the halo group is bromo, chloro or fluoro. The term "polyhaloalkyl" includes trichloromethyl; dichlorofluoromethyl; bromodichloromethyl; trifluoromethyl; tribromomethyl; 1,1,2,2-tetrachloroethyl; pentachloroethyl; 1,2-dibromo-1,2-dichloroethyl; 1,2,2-trichloroethyl; 1,1,2-trichloroethyl; 1,2,2,2-tetrachloroethyl; 2-chloro-1,2,2-tribromoethyl; 2-bromo-1,1,2-trichloroethyl; 2-bromo-1,2,2-trichloroethyl; 2-chloro-1,2-dibromoethyl; and 2-fluoro-1,1,2,2-tetrachloroethyl. The term "polyhalovinyl", as used herein, refers to polyhalovinyl wherein the halo group is bromo, chloro, or fluoro. The term "polyhalovinyl" includes trichlorovinyl; 2-bromo-1,2-dichlorovinyl; and 2-fluoro-1,2-dichlorovinyl.

The term "lower alkyl", as used herein, refers to a lower alkyl group of one to six carbon atoms. The term "lower alkoxy", as used herein, refers to a lower alkoxy group of one to six carbon atoms. The term "lower alkylthio", as used herein, refers to a lower alkylthio group of one to six carbon atoms. The term "lower haloalkyl", as used herein, refers to a lower alkyl group substituted with one to three atoms of bromine, chlorine or fluorine. The term "lower haloalkoxy", as used herein, refers to a lower alkoxy group substituted with one to three atoms of bromine, chlorine or fluorine. The term "lower alkylcarbonyl", as used herein, refers to a lower alkylcarbonyl group of two to seven carbon atoms. The term "cycloalkyl", as used herein, refers to a cycloalkyl group of three to six carbon atoms. The term "cycloalkalkyl", as used herein, refers to a cycloalkalkyl group of four to seven carbon atoms.

Specific compounds which may be used as active ingredients in compositions and methods according to the invention are set out in Examples 1 to 9 hereinafter.

Preferred compounds are those wherein, in formula A collectively or individually, y is zero; and $R^3$ and $R^4$ are lower alkyl, especially methyl; and where R is hydrogen or lower alkyl, especially methyl; and where X is cyano; and $R^1$ is $SCCl_3$ or $SCCl_2CHCl_2$.

A particularly preferred compound has the structure:

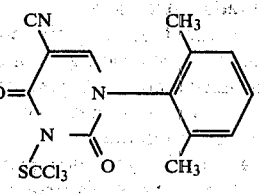

and chemical name 5-cyano-1-(2,6-dimethylphenyl)-3-trichloromethanesulphenyluracil. Its preparation is described hereinafter in Example 1.

The compositions of the invention display, variously, activity against the following diseases:

*Xanthomonas oryzae* and *Pyricularia oryzae* and other diseases on rice caused by bacteria and fungi.

Bacterial diseases of other plants such as *Xanthomonas campestris* on cabbage, *Xanthomonas vesicatoria* on peppers and *Xanthomonas malvacearum* on cotton.

Fungal diseases of other plants such as *Erysiphe graminis* on wheat and barley and other powdery mildews on various hosts such as *Sphaerotheca fuliginea* (cucurbits, e.g. cucumber), *Podosphaera leucotricha* (apples) and *Uncinula necator* (vines).

*Puccinia recondita*, *Puccinia struformis* and other rusts on wheat, *Puccinia hordei*, *Puccinia struformis* and other rusts on barley, and rusts on other hosts, e.g. coffee, apples, vegetables and ornamental plants.

The compounds are also active against other diseases such as *Botrytis cinerea* (grey mould) on tomatoes, strawberries, vines and other hosts, and *Colletotrichum coffeanum* (berry disease) of coffee.

They can be used as industrial (as opposed to agricultural) bactericides and fungicides, e.g. as paint film fungicides. The compounds also have plant growth regulating properties.

By way of example the compound of Example 1 having the structure:

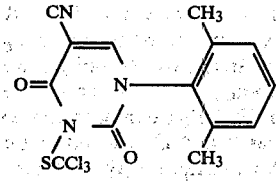

is strongly active against the diseases *Xanthomonas oryzae* and *Pyricularia oryzae*.

The active ingredients may be used as such, for example for fungicidal or bactericidal purposes, but are more conveniently formulated into compositions for such usage.

The active ingredients of the invention compositions, and salts thereof, can be applied in a number of ways, for example they can be applied, formulated or unformulated, directly to the foliage of a plant, or they can be applied to bushes and trees, to seeds or to other medium in which plants, bushes or trees are growing or are to be planted, or they can be sprayed on, dusted on or applied as a cream or paste formulation, or they can be applied as a vapour. Application can be to any part of the plant, bush or tree, for example to the foliage, stems, branches or roots, or to soil or paddy water surrounding the roots, or to the seed before it is planted.

The term "plant" as used herein includes seedlings, bushes and trees. Furthermore, the fungicidal method of the invention includes preventative, protectant, prophylactic and eradicant treatment.

In a further aspect, therefore, the present invention provides a method for combating plant pests, especially fungi and bacteria, which comprises treating plants or seeds, or their loci, with a composition according to the invention and as herein defined.

In a further aspect the invention provides a method for combating the diseases *Xanthomonas oryzae* and *Pyricularia oryzae* which comprises treating rice plants or seeds, or their locus, with the compound having the structure:

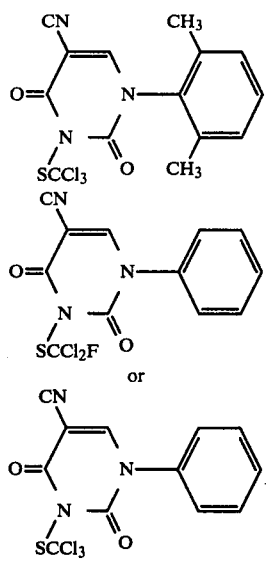

or a composition containing the same.

The active compounds may be used as such but are more conveniently formulated into compositions for use in the processes of the invention. These compositions are part of the present invention.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate their dispersion in liquids. The powders, granules or grains may also contain fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The active ingredients can be mixed in the dry state with a pyrotechnic mixture to form a composition suitable for generating in enclosed spaces a smoke containing the compounds.

Alternatively, the active ingredients may be used in a microencapsulated form.

By including suitable additives, for example additives for improving the distribution, adhesive power and resistance to rain on treated surfaces, the different compositions can be better adapted for various utilities.

The active ingredients can be used as mixtures with fertilisers (e.g. nitrogen-, potassium- or phosphorus-containing fertilisers). Compositions comprising only granules of fertiliser incorporating, for example coated with, the compound, are preferred. Such granules suitably contain up to 25% by weight of the compound.

The invention therefore also provides, in a further aspect, a fertiliser composition comprising a compound of general formula A.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethyl-cellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). When diluted to form aqueous preparations, such preparations may contain varying amounts of the active ingredient(s) depending on the intended purpose, but an aqueous preparation containing 0.0005% or 0.01% to 10% by weight of active ingredient(s) may be used.

The compositions can comprise also other compound(s) having biological activity [for example complementary fungicidal or insecticidal activity], as well as stabilising agent(s), for example epoxides (e.g. epichlorhydrin).

The compounds of formula A can be synthesized by the reaction of a 1-phenyl uracil with a polyhaloalkylsulphenyl halide or a polyhalovinylsulphenyl halide in the presence of an alkali metal. The synthesis is generally conducted by reacting an alkali metal salt of the 1-phenyl uracil in a reaction medium which may be water, an organic solvent such as an aromatic hydrocarbon, an alcohol or a halogenated hydrocarbon, or a mixture thereof with the desired sulphenyl halide. The sulphenyl halide may be diluted in an organic solvent inert to the reaction, such as a hydrocarbon or a halogenated hydrocarbon solvent, prior to addition to the reaction medium. The reaction is generally conducted at about room temperature or lower and with agitation of the reaction medium.

The 1-phenyl uracil starting materials of the following formula:

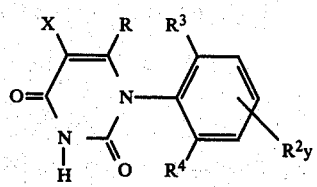

wherein R, $R^2$, $R^3$, $R^4$, X and y are as defined above, can be prepared following the methods of Senda et al., Chem. Pharm. Bull. 20(7), 1380–1388 (1972) and 22(1), 189–195 (1974).

Specific chemical substances useful as active ingredients in the compositions of the invention, and methods for preparing them, are set out in Examples 1 to 9 below. Examples 10 to 21 illustrate compositions according to the invention.

Examples 20 and 21 also illustrate methods of combating plant fungal and bacterial pests according to the invention and the activity of the active ingredients used in the invention compositions. Temperatures are given in degrees Centigrade.

EXAMPLE 1

A mixture of N-ethoxycarbonylcyanoacetamide (42 g), triethylorthoformate (40 g) and acetic anhydride (100 ml) is heated at reflux for one hour. The reaction is allowed to stand until cool and then is filtered, washing with ether, to yield α-cyano-β-ethoxy-N-ethoxycarbonylacrylamide.

To α-cyano-β-ethoxy-N-ethoxycarbonylacrylamide (1.2 g), dissolved in about 5 ml of boiling ethanol, is added 0.6 g of 2,6-dimethylaniline. The reaction is refluxed for several hours and then hexane is added. On cooling, the reaction is filtered, and washed with ethanol and ether to give α-cyano-β-(2,6-dimethylanilino)-N-ethoxycarbonylacrylamide, m.p. 138°–140°.

A mixture of α-cyano-β-(2,6-dimethylanilino)-N-ethoxy-carbonylacrylamide (1.2 g) and about 10 ml of p-cymene is heated at reflux to about 1½ hours. After cooling on standing, the crystalline product is collected by filtering and washing with ether to yield 5-cyano-1-(2,6-dimethylphenyl)uracil, m.p. 267°–269°.

To an ice cold solution of 2.40 g of sodium hydroxide in 70 ml of water is added 14.46 g (0.06 mol) of 5-cyano-1-(2,6-dimethylphenyl)uracil. Then 100 ml of dichloromethane is added. To this mixture, at 5°, is added 6.6 ml (0.06 mol) of trichloromethane sulphenyl chloride in two volumes of dichloromethane. The mixture is stirred approximately 22 min at 5°. Then the phases are separated and the organic phase is washed with ice cold water. The dichloromethane solution is dried over magnesium sulphate, filtered and stripped. The residue is triturated with ether/petane, filtered and dried to obtain the crude product, which is then purified by crystallisation to yield 5-cyano-1-(2,6-dimethylphenyl)-3-trichloromethanesulphenyluracil, m.p. 223°–225°.

The sodium salt of 5-cyano-1-phenyl-uracil is reacted with each of dichlorofluoromethane sulphenyl chloride and trichloromethane sulphenyl chloride following the foregoing procedure to yield 5-cyano-3-dichlorofluoromethane sulphenyl-1-phenyl-uracil and 5-cyano-1-phenyl-3-trichloromethane sulphenyl uracil.

EXAMPLE 2

A mixture of α-cyano-β-ethoxy-N-ethoxycarbonylacrylamide (10 g) and 45 ml of ethanol is heated to affect dissolution. Then 8.12 g of p-trifluoromethylaniline in 10 ml of ethanol is added and the mixture heated at reflux for 45 minutes. The mixture is cooled and filtered to give 14.01 g of α-cyano-β-(4-trifluoromethylanilino)-N-ethoxycarbonylacrylamide, which is added to about 60 ml of tetralin and heated at reflux for several hours. On formation of precipitate, the mixture is allowed to cool and then filtered, washed with ether, to yield 5-cyano-1-(4-trifluoromethylphenyl)uracil, m.p. 230.5°–231.5°.

To 290 mg of NaOH in 15 ml of water, cooled in an ice bath, is added 1.0 g (3.56 mol) of 5-cyano-1-(4-trifluoromethylphenyl)uracil. Then 15 ml of dichloromethane is added, followed by 0.725 ml of trichloromethanesulphenyl chloride in 1.5 ml of dichloromethane. The mixture is stirred for approximately 2 hours at 5°. Then dichloromethane and ice cold water are added and the layers separated. The organic phase is washed with ice cold water, dried over MgSO₄ and evaporated. The product is taken up with ether, filtered and washed again with ether to yield 5-cyano-3-trichloromethanesulphenyl-1-(4-trifluoromethylphenyl)uracil, m.p. 167°–168.5°.

EXAMPLE 3

Following the method of Example 2,4-fluoroaniline (0.05 mol) is reacted with α-cyano-β-ethoxy-N-ethoxycarbonylacrylamide (0.05 mol) and heated at reflux in tetralin to yield 5-cyano-1-(4-fluorophenyl)uracil, which is then reacted with trichloromethanesulphenyl chloride, in NaOH and dichloromethane, to yield the final product, 5-cyano-1-(4-fluorophenyl)-3-trichloromethanesulphenyluracil, m.p. 163°–165.5°.

In like manner, 5-cyano-1-(2,4-difluorophenyl)uracil is prepared, starting with 2,4-difluoroaniline, and is then reacted with trichloromethanesulphenyl chloride, giving 5-cyano-1-(2,4-difluorophenyl)-3-trichloromethanesulphenyluracil, m.p. 196°–198°.

EXAMPLE 4

Following the procedures hereinabove, each of 4-chloroaniline, 2,6-difluoroaniline, 4-methoxyaniline, 3-fluoroaniline, 2,6-dichloroaniline, 2,4,6-trichloroaniline, 3,4-dichloroaniline, 3,5-dichloroaniline, 2-methoxyaniline, 4-nitroaniline, 4-ethylaniline, 4-methoxy-2-methylaniline, 4-(N,N-dimethyl)aniline, 2-bromoaniline, 4-methylaniline, 4-isopropylaniline, 4-t-butylaniline, 4-acetylaniline, 2-fluoroaniline, 2-cyanoaniline, 4-methylthioaniline, 2-fluoro-4-methylaniline, 4-chloro-2-fluoroaniline, 4-fluoro-2-methylaniline, 4-trifluoromethylthioaniline, 2-chloro-4-cyanoaniline, 4-chloro-2,6-difluoroaniline, 4-chloro-2-cyanoaniline, 2,4-dimethoxyaniline, 2-chloro-6-methylaniline, 4-cyclopropylaniline, 2,6-dimethyl-4-t-butylaniline, 2,4,6-trimethylaniline, 4-chloro-2,6-dimethylaniline, 2-trifluoromethylaniline, 3,4-methylenedioxyaniline, 4-bromo-2-fluoroaniline, 2-fluoro-4-trifluoromethylaniline, 2-chloro-4-trifluoromethylaniline, and 2-methyl-4-trifluoromethylaniline is reacted with α-cyano-β-ethoxy-N-ethoxycarbonylacrylamide to yield the respective β-anilino compound. Each β-anilino compound is cyclised to yield the respective 5-cyano-1-substituted phenyl uracil under col. I, which is then reacted with trichloromethanesulphenyl chloride to yield the final product under col. II.

I 5-cyano-1-(4-chlorophenyl)uracil
5-cyano-1-(2,6-difluorophenyl)uracil
5-cyano-1-(4-methoxyphenyl)uracil
5-cyano-1-(3-fluorophenyl)uracil
5-cyano-1-(2,6-dichlorophenyl)uracil
5-cyano-1-(2,4,6-trichlorophenyl)uracil
5-cyano-1-(3,4-dichlorophenyl)uracil
5-cyano-1-(3,5-dichlorophenyl)uracil
5-cyano-1-(2-methoxyphenyl)uracil
5-cyano-1-(4-nitrophenyl)uracil
5-cyano-1-(4-ethylphenyl)uracil
5-cyano-1-(4-methoxy-2-methylphenyl)uracil
5-cyano-1-(N,N-dimethyl)phenyl)uracil
5-cyano-1-(2-bromophenyl)uracil
5-cyano-1-(4-methylphenyl)uracil
5-cyano-1-(4-isopropylphenyl)uracil
5-cyano-1-(4-t-butylphenyl)uracil
5-cyano-1-(4-acetylphenyl)uracil
5-cyano-1-(2-fluorophenyl)uracil
5-cyano-1-(2-cyanophenyl)uracil
5-cyano-1-(4-methylthiophenyl)uracil
5-cyano-1-(2-fluro-4-methylphenyl)uracil
5-cyano-1-(4-chloro-2-fluorophenyl)uracil
5-cyano-1-(4-fluoro-2-methylphenyl)uracil
5-cyano-1-(4-trifluoromethylthiophenyl)uracil
5-cyano-1-(2-chloro-4-cyanophenyl)uracil
5-cyano-1-(4-chloro-2,6-difluorophenyl)uracil
5-cyano-1-(4-chloro-2-cyanophenyl)uracil
5-cyano-1-(2,4-dimethoxyphenyl)uracil
5-cyano-1-(2-chloro-6-methylphenyl)uracil
5-cyano-1-(4-cyclopropylphenyl)uracil
5-cyano-1-(2,6-dimethyl-4-t-butylphenyl)uracil
5-cyano-1-(2,4,6-trimethylphenyl)uracil
5-cyano-1-(4-chloro-2,6-dimethylphenyl)uracil
5-cyano-1-(2-trifluoromethylphenyl)uracil
5-cyano-1-(3,4-methylenedioxyphenyl)uracil
5-cyano-1-(4-bromo-2-fluorophenyl)uracil
5-cyano-1-(2-fluoro-4-trifluoromethylphenyl)uracil
5-cyano-1-(2-chloro-4-trifluoromethylphenyl)uracil
5-cyano-1-(2-methyl-4-trifluoromethylphenyl)uracil

II 5-cyano-1-(4-chlorophenyl)-3-trichloromethanesulphenyluracil
5-cyano-1-(2,6-difluorophenyl)-3-trichloromethanesulphenyluracil
5-cyano-1-(4-methoxyphenyl)-3-trichloromethanesulphenyluracil
5-cyano-1-(3-fluorophenyl)-3-trichloromethanesulphenyluracil
5-cyano-1-(2,6-dichlorophenyl)-3-trichloromethanesulphenyluracil
5-cyano-1-(2,4,6-trichlorophenyl)-3-trichloromethanesulphenyluracil
5-cyano-1-(3,4-dichlorophenyl)-3-trichloromethanesulphenyluracil
5-cyano-1-(3,5-dichlorophenyl)-3-trichloromethanesulphenyluracil
5-cyano-1-(2-methoxyphenyl)-3-trichloromethanesulphenyluracil
5-cyano-1-(4-nitrophenyl)-3-trichloromethanesulphenyluracil
5-cyano-1-(4-ethylphenyl)-3-trichloromethanesulphenyluracil
5-cyano-1-(4-methoxy-2-methyl)-3-trichloromethanesulphenyluracil
5-cyano-1-[4-(N,N-dimethyl)phenyl]-3-trichloromethanesulphenyluracil
5-cyano-1-(2-bromophenyl)-3-trichloromethanesulphenyluracil
5-cyano-1-(4-methylphenyl)-3-trichloromethanesulphenyluracil
5-cyano-1-(4-isopropylphenyl)-3-trichloromethanesulphenyluracil
5-cyano-1-(4-t-butylphenyl)-3-trichloromethanesulphenyluracil
5-cyano-1-(4-acetylphenyl)-3-trichloromethanesulphenyluracil
5-cyano-1-(2-fluorophenyl)-3-trichloromethanesulphenyluracil
5-cyano-1-(2-cyanophenyl)-3-trichloromethanesulphenyluracil
5-cyano-1-(4-methylthiophenyl)-3-trichloromethanesulphenyluracil
5-cyano-1-(2-fluoro-4-methylphenyl)-3-trichloromethanesulphenyluracil
5-cyano-1-(4-chloro-2-fluorophenyl)-3-trichloromethanesulphenyluracil
5-cyano-1-(4-fluoro-2-methylphenyl)-3-trichloromethanesulphenyluracil
5-cyano-3-trichloromethanesulphenyl-1-(4-trifluoromethylthiophenyl)uracil
5-cyano-1-(2-chloro-4-cyanophenyl)-3-trichloromethanesulphenyluracil
5-cyano-1-(4-chloro-2,6-difluorophenyl)-3-trichloromethanesulphenyluracil
5-cyano-1-(4-chloro-2-cyanophenyl)-3-trichloromethanesulphenyluracil
5-cyano-1-(2,4-dimethoxyphenyl)-3-trichloromethanesulphenyluracil
5-cyano-1-(2-chloro-6-methylphenyl)-3-trichloromethanesulphenyluracil
5-cyano-1-(4-cyclopropylphenyl)-3-trichloromethanesulphenyluracil
5-cyano-1-(2-fluoro-4-trifluoromethylphenyl)uracil
5-cyano-1-(2-chloro-4-trifluoromethylphenyl)uracil
5-cyano-1-(2-methyl-4-trifluoromethylphenyl)uracil 5-cyano-1-(2,6-dimethyl-4-t-butylphenyl)-3-trichloromethanesulphenyluracil 5-cyano-3-trichloromethanesulphenyl-1-(2,4,6-trimethylphenyl)uracil 5-cyano-1-(4-chloro-2,6-dimethylphenyl)-3-trichloromethanesulphenyluracil 5-cyano-3-trichloromethanesulphenyl-1-(2-trifluoromethylphenyl)uracil 5-cyano-1-(3,4-methylenedioxyphenyl)-3-trichloromethanesulphenyluracil 5-cyano-1-(4-bromo-2-fluorophenyl)-3-trichloromethanesulphenyluracil 5-cyano-1-(2-fluoro-4-trifluoromethylphenyl)-3-trichloromethanesulphenyluracil 5-cyano-1-(2-chloro-4-trifluoromethylphenyl)-3-trichloromethanesulphenyluracil 5-cyano-1-(2-methyl-4-trifluoromethylphenyl)-3-trichloromethanesulphenyluracil

EXAMPLE 5

To an ice cold solution of 1.60 g (0.04 mol) of NaOH in 45 ml of water is added 9.64 g (0.04 mol) of 5-cyano-1-(2,6-dimethylphenyl)uracil, obtained as in Example 1. After dissolution, 50 ml of ice cold dichloromethane is added, followed by a solution of 9.36 g (0.04 mol) of 1,1,2,2-tetrachloroethanesulphenyl chloride (prepared by the method of U.S. Pat. No. 3,395,180) in 15 ml. of dichloromethane. The mixture is stirred for 30 min at 4°. The aqueous layer is separated and discarded. The dichloromethane solution is dried and stripped at aspirator pressure. The unreacted sulphenyl chloride is then removed by trituration with pentane/dichloromethane (4:1). The resultant crude product is purified by slurrying at 30° in 60 ml of ethanol-free chloroform, allowed to cool to RT and filtered. To the filtrate is added hexane to the cloud point, and the mixture is then filtered to yield 5-cyano-1-(2,6-dimethylphenyl)-3-(1,1,2,2-tetrachloroethanesulphenyl)uracil, m.p. 180°-183°.

The sodium salt of each of 5-cyano-1-(2-methylphenyl)uracil, 5-cyano-1-(2-chlorophenyl)uracil, 5-cyano-1-(2,6-dichlorophenyl)uracil, 5-cyano-1-(2,6-dimethylphenyl)-6-methyluracil, 5-carbamoyl-1-(2,6-dimethylphenyl)uracil and 1-(2,6-dimethylphenyl)uracil is reacted with 1,1,2,2-tetrachloroethanesulphenyl chloride to yield the respective below-listed compound:

5-cyano-1-(2-methylphenyl)-3-(1,1,2,2-tetrachloroethanesulphenyl)uracil 5-cyano-1-(2-chlorophenyl)-3-(1,1,2,2-tetrachloroethanesulphenyl)uracil 5-cyano-1-(2,6-dichlorophenyl)-3-(1,1,2,2-tetrachloroethanesulphenyl)uracil 5-cyano-1-(2,6-dimethylphenyl)-6-methyl-3-(1,1,2,2-tetrachloroethanesulphenyl)uracil 5-carbamoyl-1-(2,6-dimethylphenyl)-3-(1,1,2,2-tetrachloroethanesulphenyl)uracil 1-(2,6-dimethylphenyl)-3-(1,1,2,2-tetrachloroethanesulphenyl)uracil

EXAMPLE 6

Following the procedure of Example 1, the sodium salt of each of 5-cyano-1-(2,6-dimethylphenyl)-6-methyluracil, 5-carbamoyl-1-(2,6-dimethylphenyl)uracil and 1-(2,6-dimethylphenyl)uracil is reacted with trichloromethanesulphenyl chloride to yield 5-cyano-1-(2,6-dimethylphenyl)-6-methyl-3-trichloromethanesulphenyluracil, 5-carbamoyl-1-(2,6-dimethylphenyl)-3-trichloromethanesulphenyluracil and 1-(2,6-dimethylphenyl)-3-trichloromethanesulphenyluracil.

EXAMPLE 7

Following the procedure of Example 5, the sodium salt of 5-cyano-1-(2,6-dimethylphenyl)uracil and 5-cyano-1-(2-methylphenyl)uracil is each reacted with 2-fluoro-1,1,2,2-tetrachloroethanesulphenyl chloride to yield 5-cyano-1-(2,6-dimethylphenyl)-3-(2-fluoro-1,1,2,2-tetrachloroethanesulphenyl)uracil and 5-cyano-1-(2-methylphenyl)-3-(2-fluoro-1,1,2,2-tetrachloroethanesulphenyl)uracil.

Following the procedure of Example 1, trichloromethanesulphenyl chloride is reacted with the sodium salt of each of 5-cyano-1-(2-ethylphenyl)uracil, 5-cyano-1-(2,6-diethylphenyl)uracil and 5-cyano-1-(2-isopropylphenyl)uracil to yield 5-cyano-1-(2-ethylphenyl)-3-trichloromethanesulphenyluracil, 5-cyano-1-(2,6-diethylphenyl)-3-trichloromethanesulphenyluracil and 5-cyano-1-(2-isopropylphenyl)-3-trichloromethanesulphenyluracil.

Similarly, bromodichloromethanesulphenyl chloride is reacted with the sodium salt of 5-cyano-1-(2-methylphenyl)uracil and 5-cyano-1-(2,6-dimethylphenyl)uracil to prepare 5-cyano-1-(2-methylphenyl)-3-bromodichloromethanesulphenyluracil.

EXAMPLE 8

The sodium salt of 5-cyano-1-(2,6-dimethylphenyl)uracil is reacted with each of 1,2-dibromo-1,2-dichloroethanesulphenyl chloride and pentachloroethanesulphenyl chloride to yield 5-cyano-1-(2,6-dimethylphenyl)-3-(1,2-dibromo-1,2-dichloroethanesulphenyl)uracil and 5-cyano-1-(2,6-dimethylphenyl)-3-pentachloroethanesulphenyluracil.

Following the procedure of Example 5, trichloroethenesulphenyl chloride is reacted with sodium salt of each of 5-cyano-1-(2,6-dimethylphenyl)uracil, 5-cyano-1-(2-methylphenyl)uracil, 5-cyanol-(2-ethylphenyl)uracil and 5-cyano-1-(2,6-diethylphenyl)uracil to yield 5-cyano-1-(2,6-dimethylphenyl)-3-trichloroethenesulphenyluracil, 5-cyano-1-(2-methylphenyl)-3-trichloroethenesulphenyluracil, 5-cyano-1-(2-ethylphenyl)-3-trichloroethenesulphenyluracil and 5-cyano-1-(2,6-diethylphenyl)-3-trichloroethenesulphenyluracil.

EXAMPLE 9

The sodium salt of each of 5-cyano-1-(2,6-dimethylphenyl)uracil, 5-cyano-1-(2-methylphenyl)uracil, 5-cyano-1-(2-ethylphenyl)uracil and 5-cyano-1-(2,6-diethylphenyl)uracil is reacted with dichlorofluoromethanesulphenyl chloride using the procedure of Example 1 to yield 5-cyano-3-dichlorofluoromethanesulphenyl-1-(2,6-dimethylphenyl)uracil, m.p. 196.5°-198.5° C., 5-cyano-3-dichlorofluoromethanesulphenyl-1-(2-methylphenyl)uracil, 5-cyano-3-dichlorofluoromethanesulphenyl-1-(2-ethylphenyl)uracil, and 5-cyano-3-dichlorofluoromethanesulphenyl-1-(2,6-diethylphenyl)uracil.

EXAMPLE 10

An emulsifiable concentrate was made up by mixing the ingredients, and stirring the mixture until all the constituents were dissolved.

| | |
|---|---|
| Compound of Example 1 | 10% |
| Ethylene dichloride | 40% |

-continued

| | |
|---|---|
| Calcium dodecylbenzenesulphate | 5% |
| "Lubrol" L | 10% |
| "Aromasol" | 35% |

EXAMPLE 11

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44–100, to obtain the desired size of grains.

| | |
|---|---|
| Compound of Example 1 | 50% |
| "Dispersol" T | 25% |
| "Lubrol" APN 5 | 1.5% |
| Sodium acetate | 23.5% |

EXAMPLE 12

The ingredients were all ground together to produce a powder formulation readily dispersible in liquids.

| | |
|---|---|
| Compound of Example 1 | 45% |
| "Dispersol" T | 5% |
| "Lissapol" NX | 0.5% |
| "Cellofas" B600 | 2% |
| Sodium acetate | 47.5% |

EXAMPLE 13

The active ingredient was dissolved in a solvent and the resultant liquid was sprayed on to the granules of China clay. The solvent was then allowed to evaporate to produce a granular composition.

| | |
|---|---|
| Compound of Example 1 | 5% |
| China clay granules | 95% |

EXAMPLE 14

A composition suitable for use as a seed dressing was prepared by mixing the three ingredients.

| | |
|---|---|
| Compound of Example 1 | 50% |
| Mineral oil | 2% |
| China clay | 48% |

EXAMPLE 15

A dusting powder was prepared by mixing the active ingredient with talc.

| | |
|---|---|
| Compound of Example 5 (first made) | 5% |
| Talc | 95% |

EXAMPLE 16

A Col formulation was prepared by ball-milling the constituents set out below and then forming an aqueous suspension of the ground mixture with water.

| | |
|---|---|
| Compound of Example 1 | 40% |
| "Dispersol" T | 10% |
| "Lubrol" APN5 | 1% |
| Water | 49% |

EXAMPLE 17

A dispersible powder formulation was made by mixing together the ingredients set out below and then grinding the mixture until all were thoroughly mixed.

| | |
|---|---|
| Compound of Example 1 | 25% |
| "Aerosol" OT/B | 2% |
| "Dispersol" A.C. | 5% |
| China clay | 28% |
| Silica | 40% |

EXAMPLE 18

This Example illustrates the preparation of a dispersible powder formulation. The ingredients were mixed and the mixture then ground in a comminution mill.

| | |
|---|---|
| Compound of Example 5 (first made) | 25% |
| "PERMINAL" BX | 1% |
| "Dispersol" T | 5% |
| Polyvinylpyrrolidone | 10% |
| Silica | 25% |
| China clay | 34% |

EXAMPLE 19

The ingredients set out below were formulated into a dispersible powder by mixing the grinding the ingredients.

| | |
|---|---|
| Compound of Example 1 | 25% |
| "Aerosol" OT/B | 2% |
| "Dispersol" A | 5% |
| China clay | 68% |

In Examples 10 to 19 the proportions of the ingredients given are by weight.

There now follows an explanation of the compositions or substances represented by the various Trade Marks and Trade Names mentioned above.

| | |
|---|---|
| LUBROL L: | a condensate of nonyl phenol (1 mole) with ethylene oxide (13 moles) |
| AROMASOL H: | a solvent mixture of alkylbenzenes |
| DISPERSOL T AND AC: | a mixture of sodium sulphate and a condensate of formaldehyde with sodium naphthalene sulphonate |
| LUBROL APN 5: | a condensate of nonyl phenol (1 mole) with naphthalene oxide (5.5 moles) |
| CELLOFAS B600: | a sodium carboxymethyl cellulose thickener. |
| LISSAPOL NX: | a condensate of nonyl phenol (1 mole) with ethylene oxide (8 moles) |
| AEROSOL OT/B: | dioctyl sodium sulphosuccinate. |
| PERMINAL BX: | a sodium alkyl naphthalene sulphonate. |

EXAMPLE 20

The active ingredients (test compounds) were tested against a variety of foliar fungal diseases of plants. The technique employed was as follows.

The plants were grown in John Innes Potting Compost (No. 1, or Seed, as appropriate) in 4 cm diameter minipots. A layer of fine sand was placed at the bottom of the pot to facilitate uptake of test compound by the roots. Vermiculite was used to cover the seed in the soil tests.

The test compounds were formulated either by bead-milling with aqueous Dispersol T or as a solution in acetone/ethanol which was diluted to the required concentration immediately before use. For the foliage diseases, 100 ppm a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.05%, was added when the sprays were applied to the cereals and rusts.

For most of the tests, the test compound was applied to the soil (roots) and to the foliage (by spraying) one or two days before the plant was inoculated with the disease. After inoculation, the plants were put into an appropriate environment to allow infection to take place and then incubated until the disease was ready for assessment. The period between inoculation and assessment varied from 4 to 14 days according to the disease and environment.

The disease control was recorded by the following grading:

4 = No disease
3 = 0–5%
2 = 6–25%
1 = 26–60%
0 = >60%

The results are shown in Table I.

TABLE I

| COMPOUND NO | PUCCINIA RECONDITA (Wheat) | PYRICULARIA ORYZAE (rice) | BOTRYTIS CINEREA (tomato) |
|---|---|---|---|
| Example No. 1 | 1 | 4 | 4 |
| Example No. 3 (first compound) | 1 | 0 | 0 |
| Example No. 2 | 2 | 0 | 0 |
| Example No. 3 (second compound) | 2 | 0 | 0 |
| Example No. 5 (first compound) | 0 | 4 | 2 |
| Example No. 9 (first compound) | 0 | 4 | 1 |

The compound of Example No. 5 also displayed activity against the diseases *Venturia inaequalis* (scab on apples) and *Plasmopora viticola*.

EXAMPLE 21

This Example illustrates the control of the rice bacterial disease *Xanthomonas oryzae* according to the invention process. The test procedure is described below and thereafter, in the Table, are set out the results.

Rice seedlings at the one to two leaf stage were root drenched (10 ml) and sprayed with the chemical compound under test. Forty eight hours later the plants were inoculated by cutting off the tips of the leaves with scissors dipped in a dispersion of a billion cells/ml ($10^9$ cells/ml) of *Xanthomonas oryzae*. After 7 days at 100% relative humidity at 30° C. the seedlings were assessed for disease on a 0–4 scale, where 0 is no control, 1 is slight control, 2 is fair control, 3 is good control and 4 is complete control. Results are shown in Table II below.

TABLE II

| Compound | Rate of Application in Parts per Million (p.p.m.) | Root Drench Test | Spray Test |
|---|---|---|---|
| Example No 1 (first compound) | 50 | 4 | 4 |
|  | 10 | 3 | 3 |
|  | 5 | 2 | 3 |
| Example No. 5 (first compound) | 50 | 4 | 3 |
|  | 25 | 4 | 0 |
|  | 50 | 4 | 4 |
|  | 25 | 3 | 4 |
| Example No. 9 (first compound) | 10 | 3 | 1 |
|  | 34 |  |  |

We claim:

1. A pesticidal composition for the preventative and eradicant treatment of plant fungi and bacteria comprising a bactericidally or fungicidally effective amount of a compound of the formula

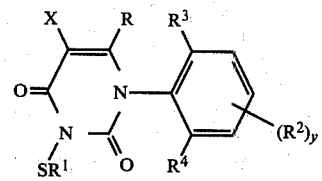

wherein
R is hydrogen, methyl or ethyl;
$R^1$ is polyhalomethyl or polyhaloethyl wherein the halo group is bromo, chloro or fluoro or polyhalovinyl wherein the halo group is bromo, chloro or fluoro;
$R^2$ is lower alkyl, lower alkoxy, bromo, chloro, fluoro, lower haloalkyl, cyano, nitro, lower alkylthio, lower alkylcarbonyl, lower alkoxycarbonyl, or cycloalkyl of 3–6 carbons;
$R^3$ is hydrogen or independently selected from the values of $R^2$;
$R^4$ is hydrogen or independently selected from the values of $R^2$;
X is hydrogen, carbamoyl or cyano; and
y is zero, one or two;
and an inert carrier.

2. The pesticidal composition of claim 1 wherein R is hydrogen; $R^1$ is $CCl_3$ or $CCl_2CHCl_2$; y is zero; X is cyano and $R^3$ and $R^4$ are lower alkyl.

3. A fungicidal and bactericidal composition for the preventative and eradicant treatment of plant fungi and bacteria comprising a bactericidally or fungicidally effective of a compound having the formula:

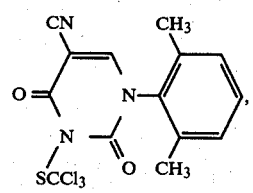

and an inert carrier.

4. A pesticidal composition for the preventative and eradicant treatment of plant fungi and bacteria comprising a bactericidally or fungicidally effective amount of a compound of the formula

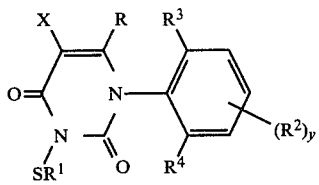

wherein

R is hydrogen, methyl or ethyl;
$R^1$ is trichloromethane, dichlorofluoromethane, 1,1,2,2-tetrachloroethane, 2-fluoro-1,1,2,2-tetrachloroethane, bromodichloromethane, 1,2-dibromo-1,2-dichloroethane, pentachloroethane and trichloroethene;
$R^2$ is hydrogen, methyl, ethyl, isopropyl, t-butyl, cyclopropyl, methoxy, bromo, chloro, fluoro, trifluoromethyl, nitro, acetyl, methylthio, trifluoromethylthio, cyano or methylenedioxy,;
$R^3$ is hydrogen, methyl, ethyl, isopropyl, chloro, fluoro, methoxy, cyano or trifluoromethyl;
$R^4$ is hydrogen, methyl, ethyl, chloro or fluoro;
X is hydrogen, carbamoyl or cyano; and
y is zero, one or two.

5. A process for the preventative and eradicant treatment of plant fungi and bacteria comprising applying to plants or seeds, or their loci, an effective amount of the composition of claim 1.

6. A process for the preventative and eradicant treatment of the diseases *Xanthomonas oryzae* and *Pyricularia oryzae* comprising applying to rice plants or seeds, or their loci, a bactericidally or fungicidally effective amount of a compound selected from the group consisting of

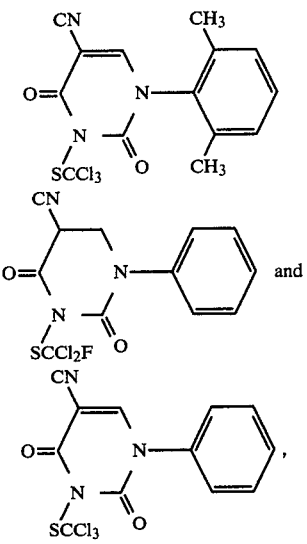

and an inert carrier.

* * * * *